United States Patent [19]
Tsao et al.

[11] Patent Number: 6,029,678
[45] Date of Patent: Feb. 29, 2000

[54] "GEL" DENTAL FLOSS

[75] Inventors: Belinda Tsao, Los Altos, Calif.;
Edward Hosung Park, Sharon, Mass.;
Paul Zwick, Stow, Ohio; Pranav Desai, Anaheim Hills, Calif.; Mingchih Michael Tseng, Hingham, Mass.;
Casper W. Chiang, Danville, Calif.

[73] Assignee: Gillette Canada Inc., Kirkland, Canada

[21] Appl. No.: 09/009,947

[22] Filed: Jan. 21, 1998

Related U.S. Application Data

[63] Continuation-in-part of application No. 08/699,891, Aug. 15, 1996, abandoned.

[51] Int. Cl.[7] .................................................. A61C 15/00
[52] U.S. Cl. ...................... 132/321; 156/180; 264/172.11
[58] Field of Search ...................................... 132/321, 323, 132/324, 325, 326, 327, 328, 329; 428/370, 373, 374; 433/11, 15, 18; 156/180, 229, 244.1; 264/172.11, 172.12, 172.13, 176.1, 210.8

[56] References Cited

U.S. PATENT DOCUMENTS

| | | | |
|---|---|---|---|
| 4,275,117 | 6/1981 | Crandall | 428/373 |
| 4,381,274 | 4/1983 | Kessler et al. | 264/147 |
| 4,424,258 | 1/1984 | Bach | 428/370 |
| 4,867,679 | 9/1989 | Rackley | 433/15 |
| 5,518,012 | 5/1996 | Dolan et al. | 132/321 |
| 5,755,243 | 5/1998 | Roberts et al. | 132/321 |

*Primary Examiner*—Gene Mancene
*Assistant Examiner*—Pedro Philogene
*Attorney, Agent, or Firm*—Chester Cekala

[57] ABSTRACT

Monofilament gel dental flosses and methods for their fabrication are provided. The gel flosses comprise a core material in combination with a gel material, where both the core and gel materials comprise thermoplastic elastomeric polymers and are sufficiently adherent to one another so as not to separate under conditions of hygienic use.

17 Claims, 6 Drawing Sheets

"GEL" DENTAL FLOSS

CROSS-REFERENCE TO RELATED APPLICATIONS

The following application is a continuation-in-part of application Ser. No. 08/699,891, filed Aug. 15, 1996, abandoned, the disclosure of which is herein incorporated by reference.

INTRODUCTION

1. Field of the Invention

The field of the invention is dental floss.

2. Background of the Invention

Tooth decay and dental disease can be caused by bacterial action resulting from plaque formation around the teeth and/or the entrapment of food particles in interstices between teeth. Removal of plaque and entrapped food particles reduces the incidence of caries, gingivitis, and mouth odors as well as generally improving oral hygiene. Conventional brushing has been found to be inadequate for removing all entrapped food particles and plaque. Therefore, to supplement brushing, dental flosses and tapes are often employed.

Traditional flosses have been fabricated from yarns of natural fibers, such as linen, silk, and cotton as well as various synthetic fibers, such as nylon. However, traditional flosses are not entirely satisfactory for a number of reasons, including their limited ability to assume thinner or thicker shapes to accommodate different sized spaces between teeth, their tendency to fray under conditions of normal use, and their lack of comfort for the user.

In order to overcome these problems with traditional flosses, efforts have been made to prepare flosses of elastomeric materials. Among other advantages, flosses prepared from such materials have the potential to assume a number of different thicknesses depending on the stress to which they are subjected, and therefore can be tailored to a user's individual needs. However, with the elastomeric flosses that have been prepared to date, when such flosses are formulated to provide sufficient softness to ensure user comfort, they become susceptible to a variety of problems, including shredding or tearing.

Accordingly, there is continued interest in the development of new elastomeric floss designs. Ideally, such designs should provide for adequate physical characteristics, such as tear or tensile strength, while at the same time provide for improved comfort to the user.

Relevant Literature

U.S. Pat. Nos. 2,677,443; 2,748,781; 3,699,979; 3,771,536; 3,800,812; 3,830,246; 3,897,795; 3,943,949; 4,033,365; 4,414,990; 4,911,927; 4,974,614; 5,076,300; 5,353,820; 5,433,226; as well as EP 0 292,673 all describe floss designs.

SUMMARY OF THE INVENTION

Monofilament gel flosses comprising a core material in combination with a gel material, as well as methods for their production, are provided. In the subject flosses, both the gel and core materials are fabricated from elastomeric materials, where the core component provides for sufficient tensile strength and the gel component provides for the softness of the floss. The gel and core thermoplastic elastomeric polymer materials are sufficiently adherent to one another to prevent separation under conditions of use. The subject flosses find use in oral hygienic applications.

BRIEF DESCRIPTION OF THE DRAWINGS

FIGS. 3a–3f are cross-sectional views, taken radially, of multicomponent coextruded filaments having cores with various cross-sections to increase the degree of adhesion between the core and sheath materials, either by increasing the surface area alone (FIGS. 3a, 3e and 3f) or by also using mechanical interlocking structures (FIGS. 3b and 3d), while

FIGS. 5a–5e are cross-sectional views of various embodiments of a floss having core filaments embedded in a gel body: an 9×10×9 tape; an 11×12×11 rod; a rod floss having five distinct groups of eight core filaments each; and a floss having 35 filaments arranged in three concentric circles surrounding a single core filament (a 16-10-8-1 configuration); all embedded in gel.

DESCRIPTION OF THE SPECIFIC EMBODIMENTS

Figure 1:
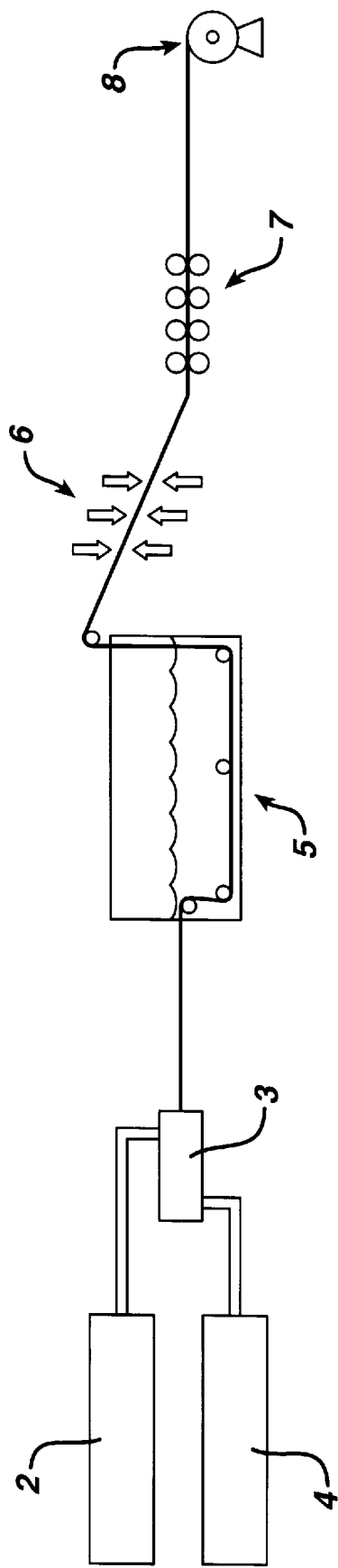
FIG. 1 is a schematic view of a horizontal production line for manufacturing a coextruded dental floss according to one embodiment of the invention.

Monofilament elastomeric gel dental flosses comprising a core material in combination with a gel material, as well as methods for their fabrication, are provided. Both the core and gel components are prepared from thermoplastic polymeric elastomeric materials which are sufficiently adherent to one another to ensure that the two components do not separate during use. In further describing the invention, the flosses will first be described in greater detail followed by a discussion of the methodologies employed for their fabrication.

Before the present dental flosses and methods for their preparation are further described, it is to be understood that the invention is not limited to the particular embodiments or extrusion methodologies described. Such flosses and methodologies may, of course, vary. It is also to be understood that the terminology is for the purpose of describing particular embodiments, and is not intended to be limiting. Instead, the scope of the present invention will be established by the appended claims.

It must be noted that as used in this specification and the appended claims, the singular forms "a", "an" and "the" include plural reference unless the context clearly dictates otherwise. Thus, for example, reference to "a polymer" includes mixtures of different polymers. Unless defined otherwise all technical and scientific terms used herein have the same meaning as commonly understood to one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

The subject dental flosses of the present invention are monofilaments comprising a core component and a gel component, where both the core and gel components are fabricated from different elastomeric materials, usually thermoplastic elastomeric materials, which are sufficiently adherent to one another so that the two components do not separate under conditions of hygienic use. The term "dental floss," as used herein, is intended to include threads, tapes, and similar configurations which are employed for cleaning by inserting between teeth. The flosses are single strands, strips etc . . . comprising the two distinct gel and core components, as opposed to two separate filaments entwined around one another. The configuration of the flosses, i.e. the spatial relationship of the core and gel components, may vary. In one embodiment, the core component is in the form a single or multiple rods or strands, encased in the gel component which acts as a sheath, where the rods or strands may have a variety of cross-sectional shapes in order to increase the surface area contact between the core and gel sheath components, where increased surface area contact may be desirable as it results in better adhesion between the sheath and core components. In other embodiments, the core component may encase the gel component. Representative embodiments of the subject flosses will be further discussed in terms of the figures below.

The dental flosses of the subject invention are sufficiently strong to withstand the stress applied during use, but sufficiently soft so as to provide comfort to the user. As such, the flosses will have an overall tensile strength which is at least about 1.5 kg, and usually at least about 2.0 kg at the optimum outer dimension. As the flosses are elastomeric, they will be able to withstand repeated stretching at room temperature to at least twice their original length and will forcibly return to approximately their original length when the tensile force is removed. The elasticity of the flosses will be such that a given length of floss will be capable of being stretched to at least 600% of its original length, usually at least about 200% of its original length, and up to about 2000% or more of its original length, where when the tensile force is removed, the floss will return to its substantially original length.

Tear resistance may also be determined by the fray test, which requires stretching the elastic floss to its maximum elongation, mounting the floss on a holder and repeatedly mechanically inserting the stretched floss between a pinch point created by two artificial "teeth," as described in parent application Ser. No. 08/699,891, the disclosure of which is herein incorporated by reference. The flosses of the subject invention are capable of withstanding more than about 10 cycles, usually more than about 20 cycles, and more usually more than about 40 cycles of insertion and retraction between the blunt "teeth" before breaking.

The outer diameter of the flosses in rod form under no tensile stress will range from about 0.04 to 0.14 inches, and usually from about 0.06 to 0.08 inches, while in tape form the thickness of the floss will range from about 0.01 to 0.1 inches, and more usually from about 0.02 to 0.05 inches while the width will range from about 0.02 to 0.2 inches and more usually from about 0.04 to 0.1 inches. In addition to the above physical characteristics, the flosses will be sufficiently soft to provide for the requisite comfort during use.

Both the core and gel materials employed in the subject flosses will be thermoplastic elastomeric materials. The preferred thermoplastic materials used for the gel and core components of the floss of this invention will generally have an elasticity above 200% and preferably above 300%. The melting points of the core and gel thermoplastic elastomeric polymers will not vary by more than about 50° F.

The core components of the flosses provide the requisite elasticity and strength characteristics to the flosses. The core component will be fabricated from an elastomeric polymeric material capable of being extruded into rods, tapes, filaments, cords, threads, or tubes and the like (hereinafter collectively referred to as "fibers"). Suitable core materials will have an overall tensile strength, as measured by ASTM method D412, of at least 500 psi, and usually at least 2000 psi. The elasticity of the core materials, as measured by ASTM 412 will be at least 200% and usually at least 400%. The core component of the subject flosses will have a shore hardness which is usually at least 20 A but less than 80 A, more usually being between 50 A and 70 A.

The core elastomeric material will usually be a blend of at least two different polymeric components, where at least one of the polymeric components is the base component and at least one of the polymeric components provides for strong adhesion of the core to the gel component of the floss. The degree of adhesion depends in part upon the chemical and structural similarity to the polymeric components of the gel portion of the floss. Polymers useful as the core component include both addition and condensation polymers. Typically, useful polymeric materials are homo- or copolymers, where the copolymers may be polymerized from 2 to 6 different monomeric units, such as homo- and copolymers of polystyrenes, polyethers block amides, polyurethanes, polyesters, polyolefins, caprylactam based polyurethanes, and the like.

Elastomeric polymers or components useful as the core include styrenic-based elastomeric copolymers. Examples of styrenic based elastomeric copolymers include SEBS, available from Shell under the tradename KRATON®, and from Consolidated Polymer Technologies (CPT) under the tradename C-Flex; SEPS (Styrene-Ethylene-Propylene-Styrene), available from M. A. Hanna; and SEP/EBS and SEPS (Styrene-Propylene-Butylene-Styrene), available from Kuraray Co. Specific non-styrenic polymers finding use include: (a) polyether block amides such as those available under the tradename PEBAX® from Elf Atochem; (b) polyurethane-based materials (thermoplastic urethanes (TPUs)), such as Tecoflex and Tecothane, both available from Thermedics Inc., PELLETHANE, available from Dow Chemical, and ELASTOLLAN, available from BASF; (c) polyester-based thermoplastic elastomers, such as HYTREL available from DuPont; (d) polyolefin-based thermoplastic elastomers, such as SARLINK® available from DSM Corp. and SANTOPRENE® available from AES Corp.; and (e) caprylactam-based polyurethanes.

Particularly preferred core component materials include: a blended material of TPU/SEPS commercially available from M.A. Hanna as HTE 2203, and a one:one blend of PEBAX® MX1205/KRATON® FG1901.

The gel component of the flosses imparts softness and, therefore, makes the flosses comfortable to use. The gel material will also have a tear resistance, as measured by the ASTM No. D412 DIE "c" tear test run at 23° C. and 20 in./min, of at least 20 pounds per linear inch (pli), or higher, where in some instances the gel material will not tear at maximum elongation under stress. The gel component of the subject flosses will have a shore hardness of no more than about 10 A, usually no more than about 5 A, where the shore hardness will generally be at least about 0 A, and more usually at least about 2 A.

The gel component will preferably comprise at least one styrenic based elastomeric polymer, in combination with at least one oil plasticizer or flexibilizer, such as a mineral oil, silicone oil, naphthenic oil, parafinic oil and the like. The ratio of elastomeric polymer to oil in the gels will typically range from about 100 parts polymer to at least 100 parts oil, usually at least 400 parts oil, where the ratio of the two components may be 100 parts polymer to as much as 2000 parts oil.

Styrenic based polymers will typically be copolymers of styrene and one or more monomers, usually olefinic monomers, where illustrative olefinic monomers include ethylene, propylene, butylene, and the like. Specific styrenic based copolymers of interest include SEPS (styrene-ethylene-propylene-styrene) copolymers, such as those sold under the trade names Septon 2006, Septon 4055, and the like.

Oils useful in the gel components include both high and low viscosity oils. By low viscosity oil it is meant that the oil has a Saybolt viscosity unit (SUS) measured by ASTM D2161, ranging from about 50 to 200, usually from about 60 to 120, and by high viscosity oil it is meant a SUS unit that ranges from about 400 to 500, and is usually at least about 350 cps. Medium viscosity oils are those oils having viscosities falling between the viscosities of the high and low viscosity oils, as defined above. Specific silicone oils of interest include those sold under the trade names Sentry Dimethicone NF 350, and the like. Mineral oils of interest include those sold under the trade names Duoprime, Kaydol, Hydrobrite, Britol, and the like.

In addition to the oil and polymer, as described above, the gel component of the subject flosses may be formulated to comprise one or more additional processing aids. Processing aids which may be present in the gel formulation include: extenders, such as waxes, resins, asphalts and the like; polyolefins, e.g. low molecular weight polyethylene, and the like; adhesives, e.g. EVA; tackifiers, e.g. alpha methyl styrene/vinyl toluene; etc. When present, such additional processing aids will make up from about 5 to 90% by weight of the gel material.

Other additives that may be present in the subject flosses through incorporation in the gel materials include coloring or pigment agents, flavoring agents, active ingredients, abrasives for improved cleaning, such as kaolin, clay, and silica, and the like. Examples of such additives are chlorhexidine (or a salt thereof), sodium fluoride, triclosan, flavor (e.g. from International Flavors and Fragrances Co. or Quest International Fragrance Inc.), fragrance, tooth desensitizer, tooth whitener, pigments, e.g., titanium dioxide, to impart color to the floss, or antioxidants, to prevent discoloration, or other additives suitable for use in dental flosses. The additive-containing component(s) may be water-soluble, to allow the additive to leach from the floss during use. The additive may also be provided as supplied, made into a microencapsulated form, or adsorbed or absorbed onto another additive, e.g., a particulate filler. Flavoring, for example, can also be released through a floss by incorporating a flavored fluid into a floss with a tubular core. The additive, if desired, can be incorporated in encapsulated form. Encapsulation may be used for thermal protection or moisture protection of the additive, and may be accomplished by any number of conventional techniques, such as spray drying, spray-chilling, drum drying or solvent evaporation. Advantageously, additives in liquid and/or encapsulated form can be incorporated into the flosses of the invention during manufacture of the filaments, rather than applying the additives later during separate coating steps. This may not only reduce the number of processing steps, but may also reduce the amount of additive needed.

The methods for adding flavor oils, for example, to the floss depend on how susceptible the materials in the floss are to breakdown by the oils, and such susceptibility is known. Convenient methods of application include those methods disclosed in U.S. patent application Ser. No. 08/738,982, entitled Particulate Modified Elastomeric Floss, Filed on Oct. 24, 1996, the disclosure of which is herein incorporated by reference.

Preferred specific gel material formulations for use in the flosses include the styrenic-based copolymers such as those available from GLS Corporation (Cary, Ill.), such as LC 115-035B, LC 115-101B, based on Kraton G-1651; SEPS gels, such as XLO141-8, -21, -22, -23, -24, -25, -26, -27, -30, -32, -34, -35,-36,-37 and -38 (available from M. A. Hanna, North Ridgeville, Ohio) described in greater detail in the experimental section below, and the like.

As mentioned above, the structural relationship between core and gel components in the flosses can vary, representative embodiments of the subject flosses will now be described in greater detail in terms of the figures. To describe the structures in the figures, the gel will be referred to as the sheath. The sheath and core may have any suitable cross-section, such as those shown in FIGS. 3a to 3g, where the core component 32 is surrounded by the sheath component 34, which components may be separated by an adhesive 33 as shown in FIG. 3c. Similar configurations exist for the tape configurations of the subject flosses, as shown in FIGS. 6a to 6d, where the core component in each configuration is labeled 62 and the sheath component is labeled 64. Multi filament core or "islands-in-the-sea" arrangements are also possible, such as depicted in FIGS. 5a–5d, where the small circles in each figure (not individually labeled) represent core components. These arrangements permit increased adhesion between the core and sheath materials by increasing their surface contact area.

Figure 3A:
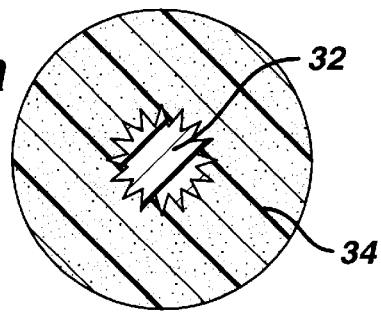
Figure 3B:
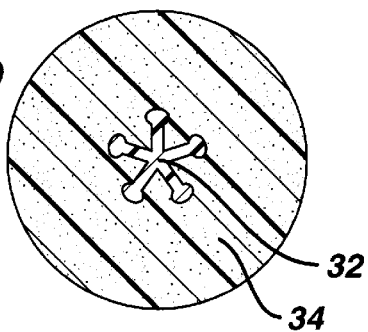
Figure 3C:
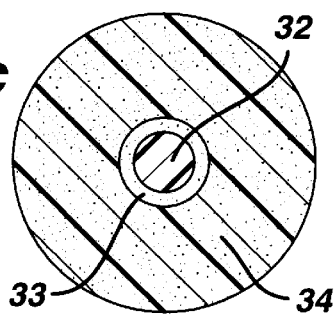
Figure 3D:
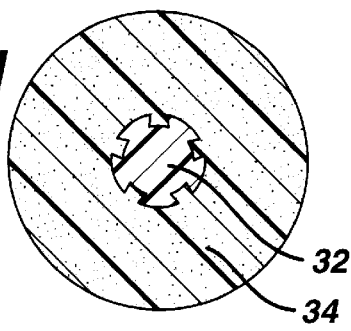
Figure 3E:
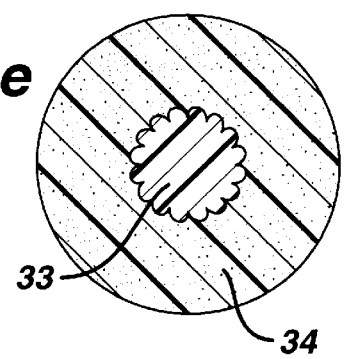
Figure 3F:
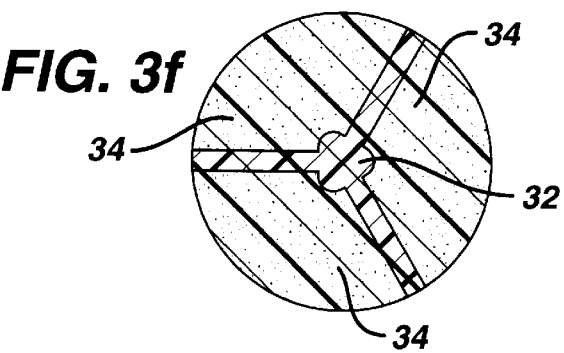
Figure 3G:
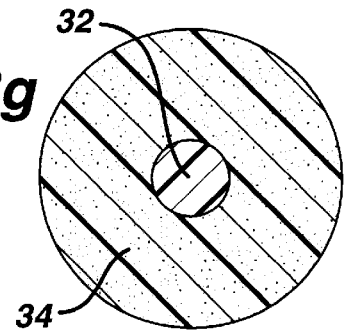
FIG. 3g shows a simple core/sheath embodiment of the subject invention.

Adhesion can also be improved between core and sheath materials either by varying the geometry of a single core to increase the surface area of contact between the core and sheath materials, as disclosed in FIGS. 3a, 3e and 3f, and by creating mechanical interlocking structures between the core and sheath materials, as disclosed in FIGS. 3b and 3d. A separate adhesive layer may also be included between the gel sheath and core to ensure adhesion between the two, as depicted in FIG. 3c, where suitable adhesive materials include EVA, a-methyl styrene/vinyl toluene, and the like.

Texturing can be added to the surface of the floss. Texturing improves the feel of floss, and increases user satisfaction with the floss because of apparent increased cleaning ability. For example, as shown in FIGS. 4c–4g, various geometries of the cross sectional areas of the monofilaments can be used, including square and triangular bumps.

Textured floss can also be created by knitting the core material to produce a bulkier, more irregular surface on which the gel is then applied, or, for a multiple filament bundle, by braiding or twisting the multiple filaments before gel-coating the bundle.

Another alternative structure for creating a floss having a textured surface is to helically-wrap one or more fine filaments around either the floss core filament or core bundle of filaments, which is then covered with the sheath material, or around the entire floss, so that the wrap material is not concealed from the user's teeth. Since the wrap material (less than about 45 denier) is small in diameter when compared to the floss' diameter (for this embodiment, less than about 0.02 inches), its only purpose being to create an irregular surface, the material must have a higher tensile and tear strength than the core material and must be capable of holding its geometry during use. Nylon or Certran have been used successfully for this purpose.

Figure 4:
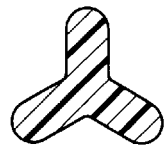
FIGS. 4–4b are cross-sectional views, taken radially, of a trilobal single component filament according to one embodiment of the invention, a trilobal multi-component filament having a sheath/core cross-section, a trilobal multicomponent filament having a tipped cross-section, and 4c–4f are cross-sectional views of filaments having four and six square bumps and four and six triangular bumps to create a textured surface, respectively.
Figure 4A:
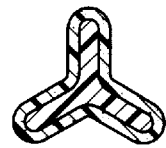
FIG. 4g is a cross-sectional view of a tube configuration comprising core and sheath components arranged around a hollow center.
Figure 4B:
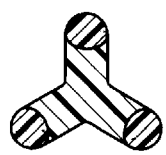

Preferred flosses may also have a "multilobal" cross-section, as shown in FIG. 4. Preferred filaments include from 3 to 8 "lobes"; one suitable filament has 3 "lobes," as shown in FIGS. 4–4b. The filaments are preferably formed by extrusion through a die having the appropriate "multilobal" cross-section. Multicomponent filaments having this cross-sectional configuration may have a sheath/core (FIG. 4a), tipped (FIG. 4b), or other suitable cross-section.

Figure 4C:
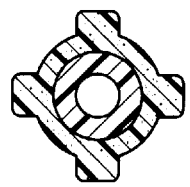
Figure 4D:
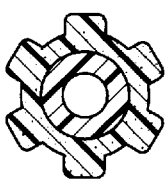
Figure 4E:
Figure 4F:
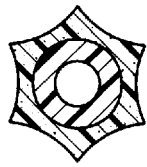
Figure 4G:
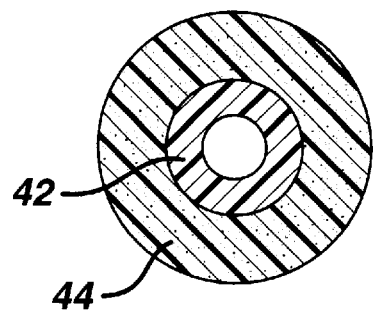
Figure 5A:
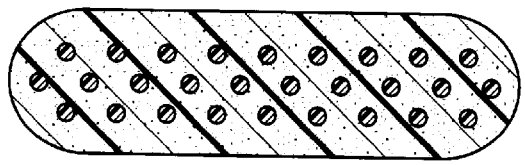
Figure 5B:
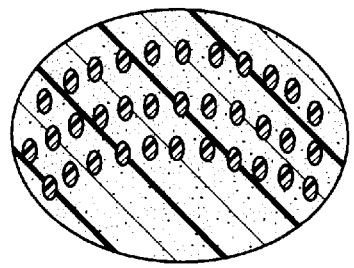
Figure 5C:
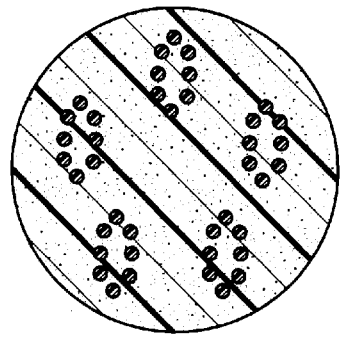
Figure 5D:
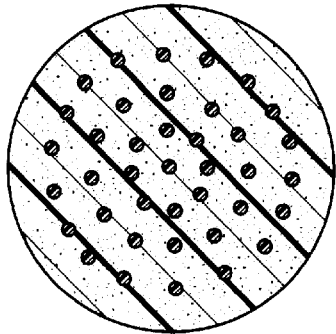

Another configuration of interest is the tube like configuration shown in FIG. 4g, in which the the sheath component 44 surrounds and core component 42 surround a hollow center.

The subject dental flosses may be prepared in a variety of ways. One method for forming a dental floss of the invention is shown schematically in FIG. 1. First, core and gel thermoplastic elastomeric materials are extruded from first and second extruders, 2 and 4 respectively to a multicomponent die assembly 3 (shown in greater detail in FIGS. 2a and 2b). The polymers are chosen to produce a floss having the desired physical properties and/or the relative cross-sections, as described above. Preferred outer diameters of the holes in the die are from about 0.04 to about 0.14 inches. The die block is fitted with heater probes and a thermocouple. The heater is set at a temperature sufficient to avoid solidifying both thermoplastic elastomeric materials.

The filament coextruded from the die 3 is then quenched by passing the filament through a quenching means 5. The quenching means 5 may be any convenient means for rapidly reducing the temperature of the coextrudate, where suitable quenching means include water baths, chilled air, and the like. The orientation of the die will dictate the location of this chamber. If the coextrudate exits the die horizontally (as depicted), then the water quenching chamber will be located directly downstream as close as possible to the spinneret, to minimize the opportunity for the horizontally-disposed filament to deform before quenching due to gravity. If the coextrudate is produced in a vertical stream, however, then deformation of the molten polymer stream due to gravity is not as great a concern, and the water bath may be placed further away, although still preferably less than two feet from the die. The monofilament fiber is guided under low tension from the extruder through the quench chamber and, upon exiting the bath, is passed over a series of tension-controlled rollers 7 before being wound-up under low tension 8. The speed of the tension rollers controls the size of the final filaments. Preferred speeds of travel of the fiber through the above process are from roughly 150 feet per minute for commercial processing. No draw-down up to 2 to 1 draw-down is necessary for these filaments.

Figure 2A:
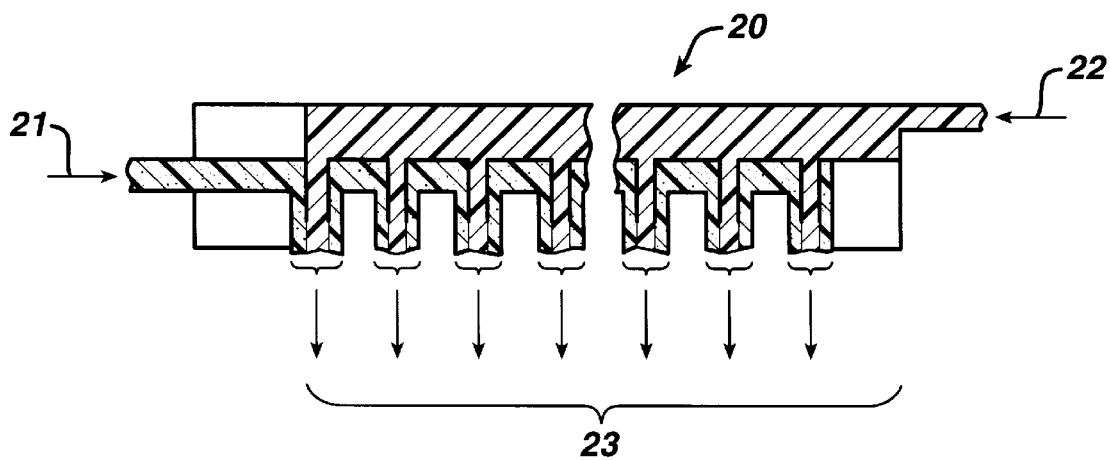
FIG. 2a is a cross-sectional view of a spinneret usable to produce multicomponent, coextruded flosses of the present invention.
Figure 2B:
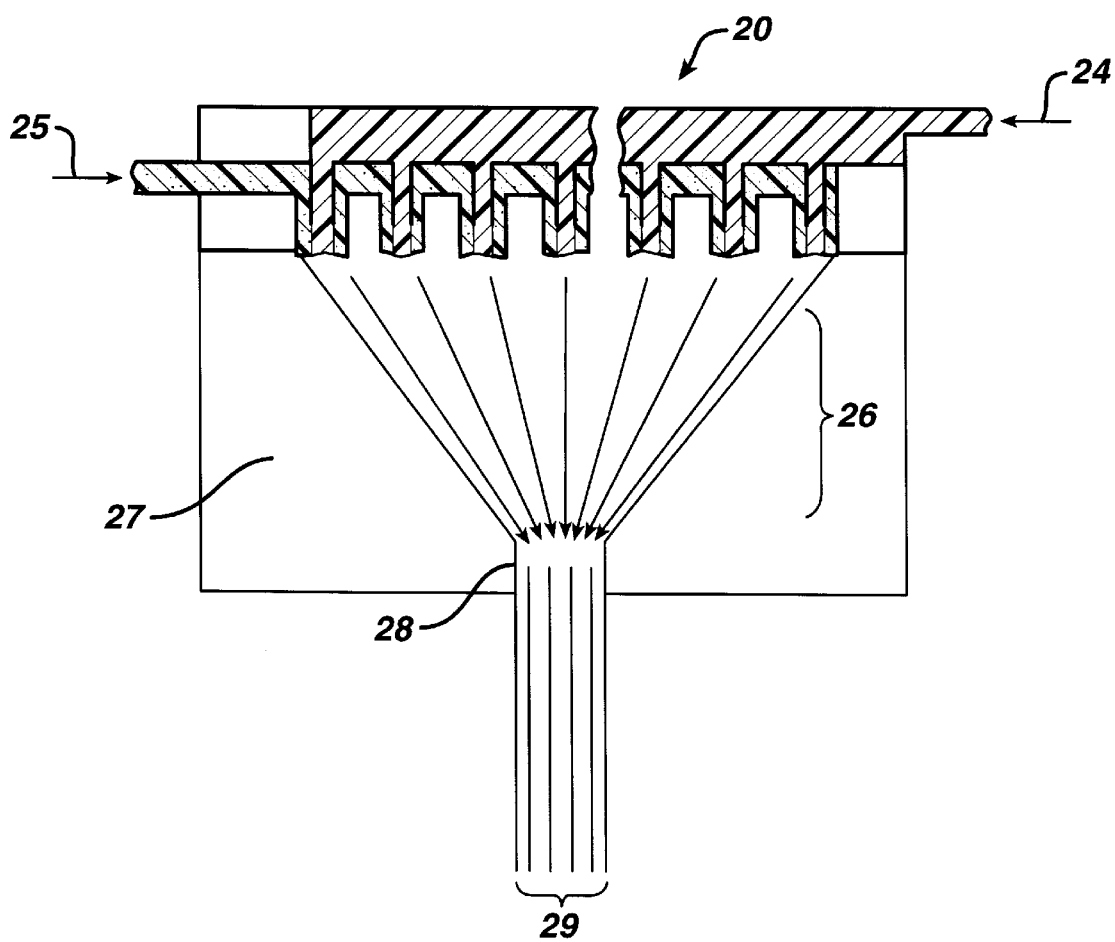
FIG. 2b shows the die-and-slot arrangement for producing the "islands-in-the-sea" tape embodiment.

FIG. 2a provides a diagram of the die 3 in greater detail. Sheath component 21 enters die 20 from one side and core component 22 enters die 20 through the oposite side, and both components are coextruded from the die 23. FIG. 2b shows a variation in which sheath component 25 and core combponent 24 enter die 20 and are coextruded through slot die 27 through slot 28 producing a monofilament having an "islands-in-the-sea" configuration 29.

In preparing gels according to the subject invention, the following considerations will be made. The strength of the subject monofilament flosses increases as the core to gel ratio increases, provided that the core component is stronger than the gel component. Depending upon the desired characteristics of the floss, it is generally preferred that at least about 20%, usually at least about 30% of the cross-sectional area of the floss be attributable to the core component. Whether a gel monofilament is suitable for flossing may be determined by focusing on tear strength and hardness of the monofilament and materials used, rather than solely on tensile strength of the resulting monofilament. As the hardness of the core material (and therefore its strength and tear resistance) increases, the desirable outer diameter of the floss should decrease, and the ratio between core and sheath should decrease, to ensure proper insertion between a user's teeth. For example, if the core thermoplastic elastomeric material in a gel floss according to the subject invention has a Shore A hardness of greater than about 35, then the outer diameter of the monofilament should be less than about 0.07 inches and the core/sheath ratio should be about 20:80. However, if the core comprises multiple filaments and the sheath material has a hardness of about 0 Shore A, then the outer diameter can be increased above 0.06 inches, depending on the cross-sectional dimensions, and can increase the core/sheath ratio above 20:80. Where the island/sea ratio is 40/60, the optimum rod outer dimension is 0.06 inches. Where the island/sea ratio is 45/55, the optimum tape dimensions are 0.036 inches×0.081 inches.

Crimped or embossed floss may be produced by passing the hot extrudate, before quenching in the water bath, through an opposing set of chilled and motorized aluminum wheels containing a textured groove. The depth of the groove is roughly half that of the extrudate, so that grooves in two opposed wheels permit the floss to pass through and be textured without substantial deformation. Patterns etched into the grooves transfer to the extrudate as it passes through the grooves while being quenched. Patterns may take any form although cross-hatched or screw-type impressions are preferred. The speed of the wheels should be set to match the extrusion speed. The wheels should be coated with teflon, or wet with water to prevent the hot extrudate from sticking to the wheels.

Alternatively, if the floss is to be crimped after the floss has already been cooled, then a heated (up to around 100° F.) grooved wheel may be used, after which the floss is requenched. The small amount of heat is sufficient to soften the outer layer of the floss to permit crimping.

If floss is braided or knitted, soft sheath material can be coated in a layer thin enough so that the outer surface of the floss has a geometry corresponding to the outer surface of the braided or knitted portion.

The following examples are offered by way of illustration and not by way of limitation. The following examples are put forth so as to provide those of ordinary skill in the art with a complete disclosure and description of how to make the monofilament flosses and carry out the extrusion methodology of the invention, and are not intended to limit the scope of what the inventors regard as their invention.

EXAMPLES

A. Equipment Set-Up

The following description of an equipment set-up and manufacturing procedure is representative of that used to create the flosses described. Two 1.25-inch diameter extruders were connected to a two-component extrusion die with metering pumps on each screw operating to deliver the flow rate of material to the die to form a floss having a desired ratio of core material:gel material. Alternatively, metering pumps can be omitted if the extrusion screws alone provide an acceptable product. The two-component extrusion die included a metering plate, a distributing plate, and a spinneret/die. Operating temperatures of the equipment and molten materials were recorded at various stages before leaving the die. After being coextruded through the extrusion die according to standard methods, the extrudate was processed with a downstream filament spinning set-up to produce floss. The downstream set-up included a quenching water bath, tension-controlled rollers and a winder. A representative set-up is also provided in FIG. 1.

B. Gel Formulations

A number of gel thermoplastic elastomers suitable for use as the gel component in the subject flosses according to the subject invention were prepared according to Table 1 and 1A, below.

TABLE 1

| Material | XL014 1-8 (%) | XL014 1-21 (%) | XL014 1-22 (%) | XL014 1-23 (%) | XL014 1-24 (%) | XL014 1-25 (%) | XL014 1-26 (%) | XL014 1-27 (%) | XL014 1-30 (%) | XL014 1-31 (%) | XL014 1-32 (%) | XL014 1-34 (%) | XL014 1-35 (%) |
|---|---|---|---|---|---|---|---|---|---|---|---|---|---|
| Septon 4055 (SEPS) | 16.8 | 16.63 | 16.44 | 22.03 | 16.44 | 24.90 | 16.6 | 11.07 | 15.97 | 15.48 | 15.97 | 15.97 | 15.97 |
| Britol 50T (High Mol. Wt. Mineral Oil) | 80.0 | | | | | | | | | | | | |
| Irganox 1010 (antiox.) | 0.1 | 0.1 | 0.1 | 0.1 | 0.1 | 0.1 | 0.1 | 0.1 | 0.1 | 0.10 | 0.10 | 0.1 | 0.1 |
| Irgafos 168 (antiox.) | 0.1 | 0.1 | 0.1 | 0.1 | 0.1 | 0.1 | 0.1 | 0.1 | 0.1 | 0.10 | 0.10 | 0.1 | 0.1 |
| Engage EG 8200 | | | | | | | | | 2.97 | 5.94 | | | |
| Exxon PP 3505 G | | | | | | | | | | | | 2.97 | 2.97 |
| Affinity SM 1300 | | | | | | | | | | | 2.97 | | |
| Affinity PL 1880 (modifier: low MWPE) | 3.0 | 2.97 | | | | | | | | | | | |
| Sentry Dimethacone NF 350 | | | | 14.85 | | | | | | | | | |
| Duoprime 90 (mix) | | | | | 41.08 | 37.35 | 41.5 | 44.27 | | | | | |
| Duoprime 90 (inject) | | | | | 41.08 | 37.35 | 41.5 | 44.27 | | | | | |
| Kemamide E (used as anantiox.) | | | .20 | 0.20 | 0.20 | 0.2 | 0.2 | 0.2 | | | | | |
| Kaydol (blend) | | | | | | | | | | | | | 39.93 |
| Kemira OR 470 | | 1.00 | 1.00 | 1.00 | 1.00 | | | | 1.00 | 1.00 | 1.00 | | |
| Kaydol (inject) | | | | | | | | | | | | | 39.93 |
| Hydrobrite 200 (mix) | | 39.60 | 41.08 | 30.86 | | | | | 39.93 | 38.69 | 39.93 | | |
| Hydrobrite 200 (side inject) | | 39.60 | 41.08 | 30.86 | | | | | 39.93 | 38.69 | 39.93 | | |

TABLE 1A

| Material | XL0141-36 (%) | XL0141-37 (%) | XL0141-38 (%) |
|---|---|---|---|
| Septon 4055 (High M.W. SEPS) | 16.72 | 16.80 | 16.63 |
| Hydrobrite 200 PO Blend (Mineral Oil) | 39.79 | 40.00 | 39.60 |
| Hydrobrite 200 PO Inject | 39.79 | 40.00 | 39.60 |
| Irganox 1010 | .10 | .10 | .10 |
| Irgafos 169 (Phosphite) | .10 | .10 | .10 |
| Kemira OR 470 | | | |
| Himont 6331 (Polypropylene) | 2.50 | | |
| AC-9A PE Wax | | 2.00 | |
| Tipure R-103 | 1.00 | 1.00 | 1.00 |
| Affinity PL 1880 | | | 2.97 |

TABLE 2

| Property XL0141- | -21 | -22 | -23 | -24 | -30 | -32 | -34 | -35 | -38 |
|---|---|---|---|---|---|---|---|---|---|
| Elongation (%) | 1000 | 1070 | 1000 | 1000 | 1170 | 1110 | 1114 | 1100 | 717 |
| 50% modulus (psi) | 15 | 4 | | 5 | 3 | 6 | 5 | 1 | — |
| 100% modulus (psi) | 22 | 7 | | 6 | 7 | 8 | 8 | 4 | 11 |
| 200% modulus (psi) | 35 | 10 | | 10 | 10 | 13 | 12 | 7 | 40 |
| 300% modulus (psi) | 49 | 15 | | 13 | 17 | 20 | 20 | 15 | 56 |
| Tensile (psi) | 184 | 67 | | 86 | 99 | 132 | 175 | 163 | 102 |
| Hardness 1 (A) (shore A) | 11 | 6 | | 6 | 6 | 7 | 6 | 7 | 9 |
| Melt Flow Rate 1 (2.16 kg @ 230° C.) | 45.74 | 328.5 | | | 105 | 52.30 | 190 | 170 | 56.3 |
| Melt Flow Rate 2 (2.16 kg @ 150° C.) | 5.5 | 14.7 | | 42 | 11.3 | 3.4 | 96 | 84 | — |
| Tension Set (100% @ 23° C.) | 3.0 | 1.5 | | 1.3 | 3.5 | 1.8 | 2.0 | 3.5 | — |
| Compression Set ((22 hrs @ 23° C.) | 7.2 | 4.7 | | 14.0 | | | | | — |
| Density (g/cm3) | .89 | .88 | | .85 | .88 | .88 | .88 | .88 | — |
| Tear Resistance (pli) | 33 | | | | 26 | 30 | | | — |

TABLE 3

Figure 6A:
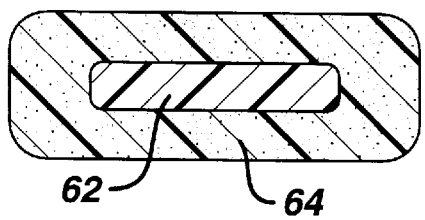
FIGS. 6a–6d are different tape configurations according to the subject invention.
Figure 6B:
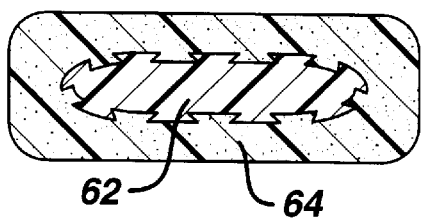
Figure 6C:
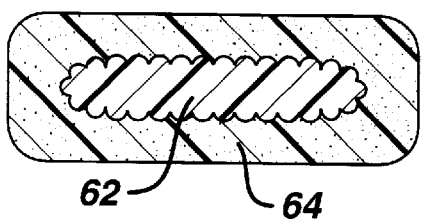
Figure 6D:
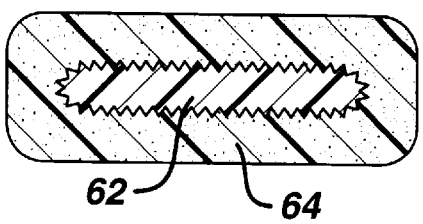

| Example No.: | 1 | 2 | 3 | 4 | 5 |
|---|---|---|---|---|---|
| Cross-section | 34 islands/sea + rod; FIG. 6b | 34 islands/sea tape | Core/sheath | Core/sheath tube; FIG. 4c | Multiple Bicomponent Filaments |
| Core Component | TPU/SEPS. HTE 2203 | TPU/SEPS. HTE 2203 | Hanna HTE 1113 (Shore A 66 SBS) | PEBAX MX1205/ KRATON FG1901 1:1 blend | Hanna TPU/KRATON blend HTE 2203 |
| Sheath Comp. | SEPS gel XL0141-8 | GLS G6713 KRATON | GLS LC 115-035B | GLS LC 115-035B | GLS KRATON G6713 |
| Ratio (Sheath/Core) | 50/50 | 50/50 | 80/20 | 80/20 | 30/70 |
| Sheath O.D./Core O.D. (in.) | Rod 0.08" O.D. | 0.0065" × 0.372" tape | 0.07"/0.032" | 0.060"/0.032"; tube 0.020" | — |
| Metering Pumps (size (cc) /speed (rpm)) | 6cc/5 rpm both | 6 cc/3 rpm both | 1 amp/19.5 rpm for sheath mat'l; no melt pump for core mat'l | 1 amp/19.5 rpm for sheath mat'l no melt pump for core mat'l | 6 cc/2.4 rpm (sheath) 6 cc/5.6 rpm (core) |
| Temp. of Core mat'l at die exit (° C.) | 201 | 199 | not measured | not measured | 196 |
| Temp. of Sheath mat'l at die exit (° C.) | 205 | 200 | not measured | not measured | 197 |
| Temp. of Spin Head (° C.) | 210 | 203 | 182 | 182 | 203 |
| Winder Speed (mpm) | 20 | Manual wind | 22.3 ft/min | approx 22 ft/min. | hand-wound |
| Fray Test (avg. of 5 runs) | 147 +/− 8 Blunt | 197 Blunt; 3.2 +/− 0.2 Sharp | 24 +/− 1 Blunt | 62 +/− 10 Blunt | 96 filaments: 32 +/− 2 cycles (Sharp) 48 filaments: 37 +/− 3 cycles (Sharp) |
| Tensile strength (kg) | 3.1 +/− 0.1 | not measured | | | |
| Comments | | 15 mm × 017 mm slot die; vertical extrusion | | | |

| Example No.: | 6 | 7 | 8 | 9 | 10 | 11 |
|---|---|---|---|---|---|---|
| Cross-section | Islands sea rod | Islands sea rod | Islands sea tape | Islands sea tape | Islands sea rod | Islands sea rod |
| Core Component | HTE 2203 | HTE 2203 | HTE 2203 | HTE 2203 | HTF 2203 | HTE 2203 |
| Sheath Comp. | XL-0141-38 | XL-0141-38 | XL-0141-38 | XL-0141-38 | XL-l041-38 | XL-1041-38 |
| Ratio (Sheath/Core) | 35/65 | 44/56 | | 45/55 | 37/63 | 35/65 |
| Sheath O.D./Core O.D. (in.) | .060"/ | .058"/ | .087"/.037" | .076"/.035" | | |
| Metering Pumps (size (cc)/ speed (rpm)) | | | | | | |
| Temp. of Core mat'l at die exit (° C.) | 410° F. | 360° F. | 415° F. | 360° F. | 425° F. | 390° F. |
| Temp. of Sheath mat'l at die exit (° C.) | 360° F. | 350° F. | 360° F. | 360° F. | 360° F. | 360° F. |
| Temp. of Spin Head (° C.) | | | | | | |
| Winder Speed (mpm) | | | | | | |
| Fray Test (avg. of 5 runs) | | | | | | |
| Tensile strength (kg) | | | | | | |
| Comments | | | | | | |

It is evident from the above results and discussion that improved elastomeric floss materials are provided. The subject two component monofilament floss configurations result in a floss material with adequate physical characteristics, e.g. tensile strength, fray resistance, and softness to ensure effective and pleasurable use.

Other embodiments are within the claims. For example, while bicomponent monofilaments have been described above in the Detailed Description, the filaments could contain any desired number of components, and in this case would be manufactured by extrusion through a suitable multicomponent die using the appropriate number of extruders.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An elastomeric dental floss comprising:
   a monofilament comprising a core elastomeric material and a gel thermoplastic elastomeric material, wherein said core and gel materials adhere to each other.

2. The floss according to claim 1, wherein said gel elastomeric material comprises a styrenic based copolymer.

3. The floss according to claim 1, wherein said core elastomeric material comprises a styrenic based copolymer.

4. The floss according to claim 1, wherein the melting points of said core and gel materials differ by less than 50° F.

5. The floss according to claim 1, wherein said core material is encased in said gel material.

6. An elastomeric dental floss comprising:
   a monofilament comprising a core elastomeric material and a gel thermoplastic elastomeric material, wherein each of said core and gel thermoplastic materials comprises a styrenic based copolymer.

7. The floss according to claim 6, wherein said gel elastomeric material further comprises an oil.

8. The floss according to claim 7, wherein said oil is selected from the group consisting of silicone oil, mineral oil, napthenic oil and paraphenic oil.

9. The floss according to claim 6, wherein the melting points of said core and gel materials do not differ by more than 50° F.

10. An elastomeric dental floss comprising:
a monofilament comprising a core thermoplastic elastomeric material encased in a gel thermoplastic elastomeric material, wherein said core and gel materials comprise styrenic based copolymers and said gel material further comprises an oil.

11. The floss according to claim 10, wherein the melting points between said core and gel materials do not differ by more than 50° F.

12. The floss according to claim 10, wherein said gel material has a Shore A hardness of no more than about 10 A.

13. The floss according to claim 10, wherein said core thermoplastic elastomeric material comprises a blend of thermoplastic urethane and styrene-ethylene-propylene-styrene.

14. The floss according to claim 10, wherein said styrenic based copolymer of said gel material comprises styrene-ethylene-propylene-styrene.

15. A method of producing a monofilament gel dental floss comprising a core thermoplastic elastomeric material in combination with a gel thermoplastic elastomeric material, said method comprising:

coextruding said core and gel thermoplastic elastomeric materials through a multicomponent die assembly to form a coextrudate comprising said core thermoplastic elastomeric material in combination with said gel thermoplastic elastomeric material; and quenching said coextrudate.

16. The method according to claim 15, wherein said core and gel materials comprise styrenic based copolymers.

17. The method according to claim 15, wherein the melting points of said core and gel materials do not differ by more than 50° F.

* * * * *